(12) United States Patent
Schromm et al.

(10) Patent No.: US 6,197,824 B1
(45) Date of Patent: Mar. 6, 2001

(54) BENZAMIDINE DERIVATIVES AND THE USE THEREOF AS MEDICAMENTS WITH LTB4-ANTAGONISTIC EFFECT

(75) Inventors: Kurt Schromm, Ingelheim; Ralf Anderskewitz, Bingen; Ernst-Otto Renth, Kiel; Franz Birke, Ingelheim; Hans Michael Jennewein, Wiesbaden; Christopher John Montague Meade, Bingen, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/242,389

(22) PCT Filed: Sep. 9, 1997

(86) PCT No.: PCT/EP97/04921

§ 371 Date: Jun. 2, 2000

§ 102(e) Date: Jun. 2, 2000

(87) PCT Pub. No.: WO98/11062

PCT Pub. Date: Mar. 19, 1998

(30) Foreign Application Priority Data

Sep. 10, 1996 (DE) .................................... 196 36 689

(51) Int. Cl.⁷ ...................... A61K 31/155; C07C 257/18
(52) U.S. Cl. ........................ 514/637; 564/244; 564/229; 514/633
(58) Field of Search .................................. 514/637, 633; 564/244, 229

(56) References Cited

U.S. PATENT DOCUMENTS 5,246,965  9/1993  Main .
5,731,332 * 3/1998  Anderskewitz et al. ............. 514/354

FOREIGN PATENT DOCUMENTS

| 44 24 713A1 | 1/1996 | (DE) . |
| 195 46 452A1 | 6/1997 | (DE) . |
| 0 496 378A1 | 7/1992 | (EP) . |
| 0 518 818A1 | 12/1992 | (EP) . |
| 0 574 808A1 | 12/1993 | (EP) . |
| WO93 16036A1 | 8/1993 | (WO) . |

* cited by examiner

Primary Examiner—Charanjit S. Aulakh
(74) Attorney, Agent, or Firm—Robert P. Raymond; Alan R. Stempel; Mary-Ellen M. Devlin

(57) ABSTRACT

Novel benzamidines, having LTB4-antagonistic activity, of the formula

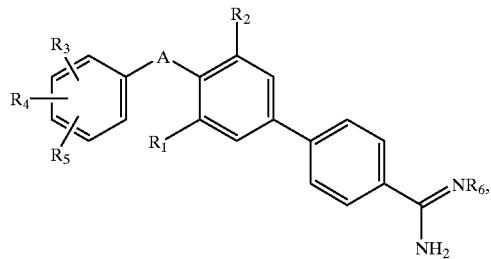

(1)

methods for their preparation, their and their use as medicaments.

9 Claims, No Drawings

BENZAMIDINE DERIVATIVES AND THE USE THEREOF AS MEDICAMENTS WITH LTB4-ANTAGONISTIC EFFECT

RELATED APPLICATIONS

This application is filed pursuant to 35 U.S.C. 371 and claims benefit under 35 USC 120 PCT/EP97/04921 filed Sep. 9, 1997.

The present invention relates to new benzamidine derivatives, processes for preparing them and their use in pharmaceutical compositions. The new benzamidine derivatives correspond to general formula 1

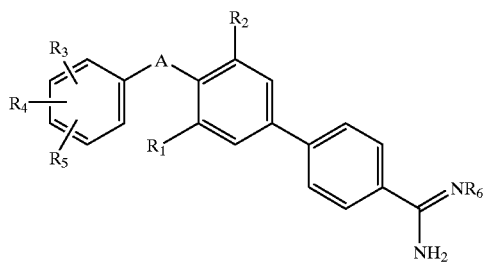

(1)

wherein

A denotes —O—$C_{2-4}$-alkylene-O— or —$C_{1-3}$-alkylene-O—

$R_1$ denotes branched or unbranched $C_{1-6}$-alkyl, branched or unbranched $C_{3-6}$-alkenyl, preferably allyl or F, Cl, Br, I;

$R_2$ denotes hydrogen, branched or unbranched $C_{1-6}$-alkyl, branched or unbranched $C_{3-6}$-alkenyl, preferably allyl or F, Cl, Br, I;

$R_3$ and $R_4$, which may be identical or different, independently of one another denote hydrogen, branched or unbranched $C_{1-6}$-alkyl, branched or unbranched $C_{3-6}$-alkenyl, preferably allyl, $C_{1-6}$-alkoxy, ($C_{1-4}$-alkyl)OC(O)O—, OH or $CF_3$ or together denote a fused-on mono- or fused bi-cyclic ring system which is completely or partially conjugated and optionally contains one or two heteroatoms from the group oxygen, sulphur or nitrogen, and which may be optionally substituted by OH, $C_{1-4}$-alkoxy or $C_1$–$C_4$-alkyl;

$R_5$ denotes hydrogen, aryl, preferably phenyl, —O-phenyl, —$CR_7R_8$-phenyl, —C(O)phenyl, —$SO_2$phenyl, —CH(OH)phenyl, wherein the phenyl ring may be substituted by OH, —$C_{1-4}$-alkoxy, or it denotes —C(O)$NR_9R_{10}$;

$R_6$ denotes hydrogen, $C_{1-6}$-alkoxycarbonyl, ($C_{1-5}$-alkyl)-carbonyl or —C(O)—O—($C_{1-6}$-alkylene)-$NR_{11}R_{12}$;

$R_7$ and $R_8$, which may be identical or different, denote hydrogen, branched or unbranched $C_{1-8}$-alkyl, or $CF_3$;

$R_9$ and $R_{10}$, which may be identical or different, independently of one another denote hydrogen, branched or unbranched $C_{1-8}$-alkyl;

$R_{11}$ and $R_{12}$, which may be identical or different, independently of one another denote hydrogen, branched or unbranched $C_{1-8}$-alkyl;

optionally in the form of the individual optical isomers, mixtures of the individual enantiomers or racemates and in the form of the free bases or the corresponding acid addition salts with pharmacologically acceptable acids.

Preferred compounds of general formula 1 are those wherein

A denotes —$OCH_2CH_2O$—, —$CH_2O$—, —$CH_2CH_2CH_2O$—;

$R_1$ denotes branched or unbranched $C_{1-5}$-alkyl, allyl;

$R_2$ denotes hydrogen;

$R_3$ denotes hydrogen, $C_{1-6}$-alkyl, $OCH_3$, $C_2H_5OC(O)O$—, OH, Cl, F, $CF_3$;

$R_4$ denotes hydrogen, —$OCH_3$, OH;

$R_3$ and $R_4$ together denote a fused-on benzene ring, 3,4-dihydrocoumarin or 1,3-dioxolane which may be substituted by OH, $C_1$–$C_3$-alkyl or $OCH_3$;

$R_5$ denotes hydrogen, phenyl, O-phenyl, —$CR_7R_8$-phenyl, —$SO_2$phenyl, wherein the phenyl ring may be substituted by OH or $OCH_3$, or it denotes —C(O)$NR_9R_{10}$;

$R_6$ denotes hydrogen or $C_{1-4}$-alkoxycarbonyl or —C(O)—O($CH_2$)$_2$—N($C_2H_5$)$_2$;

$R_7$ and $R_8$, which may be identical or different, independently of one another denote hydrogen, $CH_3$ or $CF_3$;

$R_9$ and $R_{10}$, which may be identical or different, denote hydrogen, branched or unbranched $C_1$–$C_8$-alkyl.

Unless specifically stated otherwise the general definitions are used as follows:

$C_{1-8}$-alkyl, $C_{1-5}$-alkyl and $C_{1-4}$-alkyl generally denote a branched or unbranched hydrocarbon group having 1 to 4 or 5 or 8 carbon atoms, which may optionally be substituted with one or more halogen atoms—preferably fluorine—which may be the same as or different from each other. The following hydrocarbon groups are mentioned by way of example:

methyl,ethyl, propyl, 1-methylethyl (isopropyl), n-butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2,-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless otherwise specified, lower alkyl groups having 1 to 4 carbon atoms such as methyl, ethyl, propyl, iso-propyl, n-butyl, 1-methylpropyl, 2-methylpropyl or 1,1-dimethylethyl are preferred.

Accordingly, alkylene denotes a branched or unbranched double-bonded hydrocarbon bridge having 1 to 8 carbon atoms which may optionally be substituted with one or more halogen atoms—preferably fluorine—which may be the same as or different from each other.

Aryl generally denotes an aromatic group having 6 to 10 carbon atoms—as well as in compositions, where the aromatic group may be substituted by one or more lower alkyl groups, trifluoromethyl groups, cyano groups, alkoxy groups, nitro groups, amino groups and/or one or more halogen atoms, which may be identical to or different from one another; the preferred aryl group is an optionally substituted phenyl group, whilst the preferred substituents are halogen—such as fluorine, chlorine or bromine—and hydroxyl.

Alkoxy generally denotes a straight-chained or branched hydrocarbon group having 1 to 8 carbon atoms, bound via an oxygen atom. A lower alkoxy group having 1 to 3 carbon atoms is preferred. The methoxy group is particularly preferred.

As has been found, the compounds of formula 1 are characterised by their wide range of possible applications in the therapeutic field. Particular mention should be made of those applications in which the $LTB_4$-receptor-antagonistic properties play a part. Examples include, in particular:

arthritis, asthma, chronic obstructive lung diseases, such as chronic bronchitis, psoriasis, ulcerative colitis, gastropathy or enteropathy induced by nonsteroidal antiinflammatories, cystic fibrosis, Alzheimer's disease, shock, reperfusion damage/ischaemia, atherosclerosis and multiple sclerosis.

The new compounds may also be used to treat diseases or conditions in which the passage of cells from the blood through the vascular endothelium into the tissues is of importance (such as metastasis) or diseases and conditions in which the combination of $LTB_4$ or another molecule (such as 12-HETE) with the $LTB_4$-receptor influences cell proliferation (such as chronic myeloid leukaemia).

The new compounds may also be used in combination with other active substances, e.g. those which are used for the same indications, or for example with antiallergics, secretolytics, $\beta_2$-adrenergics, inhaled steroids, antihistamines and/or PAF-antagonists. They may be administered by topical, oral, transdermal, nasal or parenteral route or by inhalation.

The activity ratios may be investigated pharmacologically and biochemically using tests such as those described in WO 93/16036, pp. 15 to 17—the contents of which are referred to herein.

The therapeutic or prophylactic dose depends not only on the potency of the individual compounds and the body weight of the patient but also on the nature and gravity of the illness. For oral administration the dose is between 10 and 500 mg, preferably between 20 and 250 mg. For inhalation the patient is given between about 0,5 and 25 mg, preferably between about 2 and 20 mg of active substance.

Inhalable solutions generally contain between about 0.5 and 5% of active substance. The new compounds may be administered in conventional preparations, e.g. as plain or coated tablets, capsules, lozenges, powders, granules, solutions, emulsions, syrups, inhalable aerosols, ointments or suppositories.

The Examples which follow show some possible ways of formulating the preparations:

FORMULATION EXAMPLES
1. Tablets

| Composition: | |
|---|---|
| Active substance according to invention | 20 parts by weight |
| Stearic acid | 6 parts by weight |
| Glucose | 474 parts by weight |

The ingredients are processed in the usual way fo form tablets weighing 500 mg. If desired the content of active substance may be increased or reduced and the quantity of glucose reduced or increased accordingly.

2. Suppositories

| Composition: | |
|---|---|
| Active substance according to invention | 100 parts by weight |
| Lactose, powdered | 45 parts by weight |
| Cocoa butter | 1555 parts by weight |

The ingredients are processed in the usual way to form suppositories weighing 1.7 g.

3. Powder for Inhalation

Micronised active substance powder (compound of formula 1; particle size about. 0.5 to 7 $\mu$m) is packed into hard gelatin capsules in a quantity of 5 mg, optionally with the addition of micronised lactose. The powder is inhaled from conventional inhalers, e.g. according to DE-A 33 45 722, which is referred to herein.

The new compounds may be prepared using the following conventional methods, which are known from the prior art:

1. Reduction of an amidoxime of general formula 2

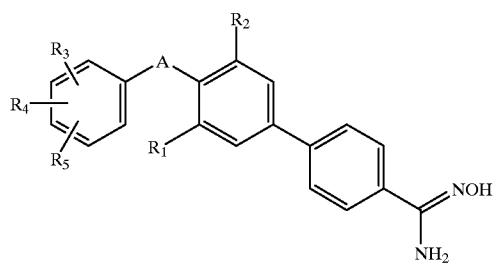

(2)

wherein $R_1$ to $R_5$ and A are as hereinbefore defined.

The reduction of the amidoxime may conveniently be carried out by catalytic hydrogenation, especially with Raney nickel in a lower alcohol, e.g. methanol.

The amidoxime of the formula 2 is conveniently dissolved in methanol with the addition of the calculated amount of the particular acid, the salt of which is the desired end product, and hydrogenated at ambient temperature under gentle pressure, e.g.at 5 bar, until the uptake of hydrogen has ceased.

2. Reaction of imidoesters of general formula 3

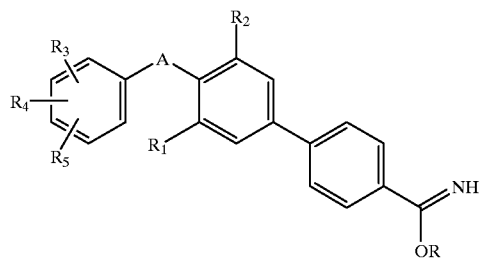

(3)

wherein $R_1$ to $R_5$ and A are as hereinbefore defined and R preferably denotes a lower alkyl group, with ammonia.

The reaction is conveniently carried out in an organic solvent at temperatures between about 0° C. and the boiling temperature of the reaction mixture, preferably between ambient temperature and about 100° C. or boiling temperature, if this is lower. Suitable solvents are polar solvents such as methanol, ethanol and propanols.

3. Reaction of a phenol of general formula 4

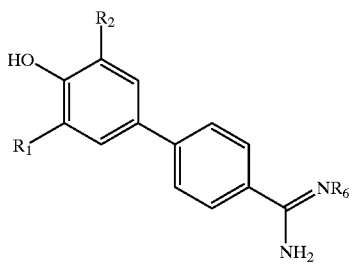
(4)

wherein $R_1$, $R_2$, $R_6$ are as hereinbefore defined, with a compound of formula 5

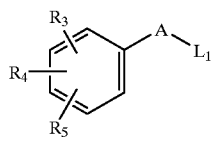
(5)

wherein A, $R_3$, $R_4$ and $R_5$ are as hereinbefore defined and $L_1$ denotes a nucleofugal leaving group such as a halogen atom or a sulphonic acid group.

The reaction is carried out in aprotic solvents such as dimethyl sulphoxide, dimethylformamide, acetonitrile or alcohols such as methanol, ethanol or propanol with the addition of a base (preferably an alkali metal or alkaline earth metal carbonate, hydroxide or hydride) at temperatures of between about 0 and 140° C. or the boiling temperature of the reaction mixture.

4. Reaction of an amidine of general formula 6

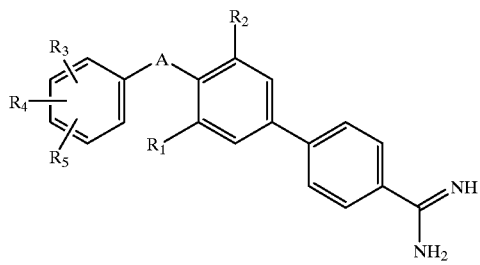
(6)

wherein $R_1$ to $R_5$ and A are as hereinbefore defined, with a compound of formula 7

(7)

wherein $R_6'$ has the same meanings as $R_6$, with the exception of H, and $L_2$ denotes a nucleofugal leaving group such as a halogen atom (such as Cl or Br) or acyloxy.

The reaction is conveniently carried out in a solvent such as tetrahydrofuran, methylene chloride, chloroform or dimethylformamide, preferably in the presence of a base such as sodium carbonate, potassium carbonate or sodium hydroxide solution or in the presence of a tertiary organic base such as triethylamine, N-ethyl-diisopropylamine, N-methylmorpholine or pyridine, which may simultaneously serve as solvents, at temperatures between −30 and 100° C., but preferably at temperatures between −10 and 80° C.

The compounds according to the invention may be prepared from compounds known from the prior art, inter alia using the methods described in the following Examples. Various other embodiments of the processes will become apparent to the skilled person from the specification. However, it is expressly pointed out that these Examples and the associated description are intended solely as an illustration and must not be regarded as limiting the invention.

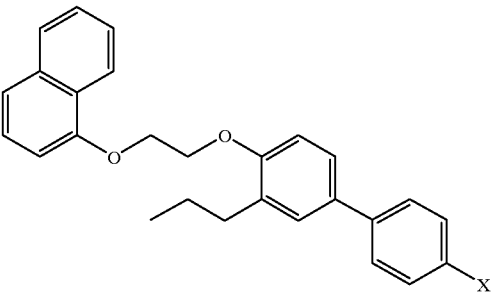

Amidoxime: $X=C(=NOH)NH_2$ 5.3 g of the nitrile of the above formula (X=CN) is refluxed together with 98 ml of ethanol, 3.65 g of hydroxylamine x HCl, 2.9 g of $Na_2CO_3$ and 21 ml of water for 5 hours. Then the mixture is distilled to dryness and the residue is stirred with water and suction filtered. 5.7 g are suspended in 25 ml of acetonitrile and mixed with 0.85 ml of methanesulphonic acid, heated and cooled again.

After suction filtering 6.4 g of the methanesulphonate are obtained in the form of white crystals.

Amidine: $X=C(=NH)-NH_2$ 6.4 g of the amidoxime ($X=C(=NOH)-NH_2$) in the form of the methanesulphonate are dissolved in 100 ml of methanol and hydrogenated, using Raney nickel as catalyst, under normal conditions, until 100% hydrogen uptake has occurred. After suction filtering, the filtrate is evaporated down and the residue is recrystalled from methanol. Yield: 3.8 g of the amidine compound as the methanesulphonate. Mp. 228–30° C.

Ethoxycarbonylamidine: $X=C(NCOOC_2H_5)-NH_2$ 2.6 g of the amidine methanesulphonate ($X=C(=NH)-NH_2$) are suspended with 1.6 ml of triethylamine in 50 ml of ethyl acetate and 0.6 ml of ethyl chloroformate in 5.5 ml of ethyl acetate is added thereto at ambient temperature over about 15 minutes. The reaction mixture is then washed three times with water, dried with $Na_2SO_4$ and evaporated down. After recrystallisation from acetonitrile the ethoxycarbonylamidine compound is obtained, mp. 142–144° C.

Following these procedures, the following compounds are obtained, for example:

| No. | compound | salt form | Mp. [° C.] |
|---|---|---|---|
| 1 | 3-propyl-4-methoxyphenyl compound | methane sulphonate | 221–223 |
| 2 | 3-propyl-4-(trifluoromethyl)phenyl compound | methane sulphonate | 212–213 |
| 3 | 4-hydroxyphenyl compound | methane sulphonate | 219–222 |
| 4 | naphthalen-2-yl compound | methane sulphonate | >230 |
| 5 | 2-propylphenyl compound | methane sulphonate | 185–188 |

-continued

| No. | compound | salt form | Mp. [° C.] |
|---|---|---|---|
| 6 | | methane sulphonate | 228–230 |
| 7 | | methane sulphonate | |
| 8 | | methane sulphonate | 211–213 |
| 9 | | methane sulphonate | 206–208 |

-continued

| No. | compound | salt form | Mp. [° C.] |
|---|---|---|---|
| 10 | | methane sulphonate | 201–203 |
| 11 | | methane sulphonate | 207–211 |
| 12 | | methane sulphonate | 212–214 |
| 13 | | methane sulphonate | 225–227 |

-continued

| No. | compound | salt form | Mp. [° C.] |
|---|---|---|---|
| 14 | | | |
| 15 | | | |
| 16 | | | |
| 17 | | methane sulphonate | 188–190 |

-continued

| No. | compound | salt form | Mp. [° C.] |
|---|---|---|---|
| 18 | | | |
| 19 | | methane sulphonate | >230° |
| 20 | | | |
| 21 | | | |

-continued

| No. | compound | salt form | Mp. [° C.] |
|---|---|---|---|
| 22 | 4-[3-propyl-4-[2-[4-[1-methyl-1-(4-hydroxyphenyl)ethyl]-2-propylphenoxy]ethoxy]phenyl]benzamidine | | |
| 23 | 4-[3-propyl-4-[2-(3-hydroxy-2-propylphenoxy)ethoxy]phenyl]benzamidine | | |
| 24 | 4-[3-propyl-4-[2-(2-hydroxyphenoxy)ethoxy]phenyl]benzamidine | | |
| 25 | 4-[3-propyl-4-[2-(3-methoxy-2-propylphenoxy)ethoxy]phenyl]benzamidine | | |

-continued

| No. | compound | salt form | Mp. [° C.] |
|---|---|---|---|
| 26 | | methane sulphonate | 188–190 |
| 27 | | methane sulphonate | 216–219 |
| 28 | | methane sulphonate | 219–222 |
| 29 | | methane sulphonate | 176 |
| 30 | | methane sulphonate | 212–213 |

-continued

| No. | compound | salt form | Mp. [° C.] |
|---|---|---|---|
| 31 | | methane sulphonate | 196–200 |
| 32 | | | 158–160 |
| 33 | | methane sulphonate | 221–223 |
| 34 | | methane sulphonate | 230 |

-continued

| No. | compound | salt form | Mp. [° C.] |
|---|---|---|---|
| 35 | | methane sulphonate | 185–188 |
| 36 | | methane sulphonate | 228–230 |
| 37 | | methane sulphonate | 233–234 |
| 38 | | methane sulphonate | 211–213 |
| 39 | | methane sulphonate | 201–203 |

-continued

| No. | compound | salt form | Mp. [° C.] |
| --- | --- | --- | --- |
| 40 | | methane sulphonate | 212–214 |
| 41 | | methane sulphonate | 230 |
| 42 | | methane sulphonate | 206–208 |
| 43 | | | 84–86 |

-continued
| No. | compound | salt form | Mp. [° C.] |
|---|---|---|---|
| 44 | 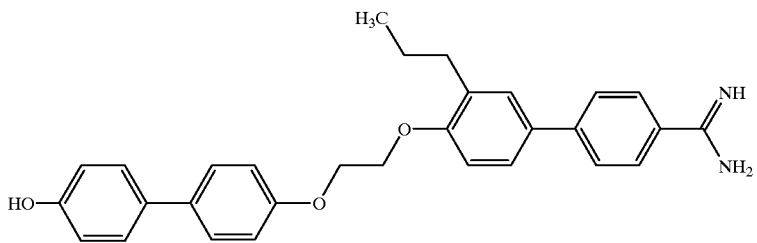 | methane sulphonate | 225–227 |
| 45 | 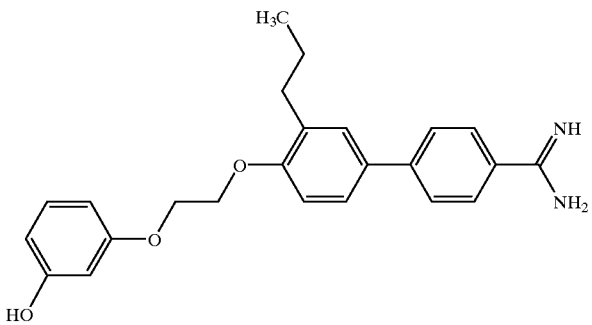 | methane sulphonate | 207–211 |
| 46 | 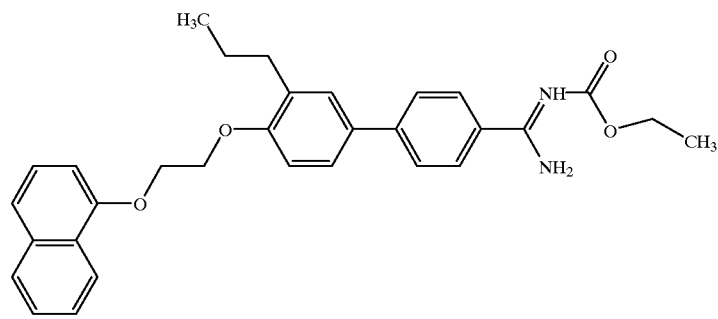 | | 142–144 |
| 47 | 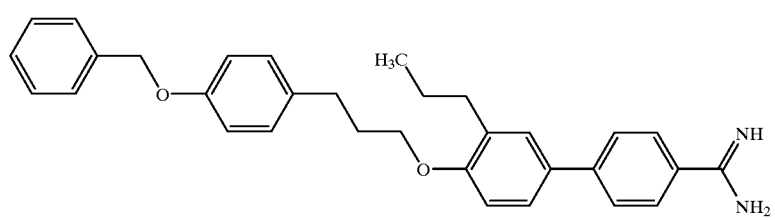 | methane sulphonate | 215–221 |
| 48 | 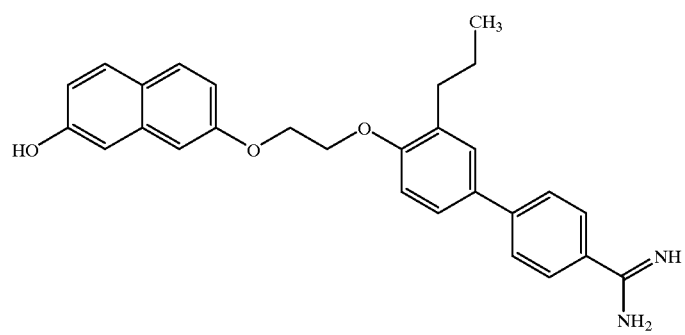 | methane sulphonate | 209–211 |

-continued

| No. | compound | salt form | Mp. [° C.] |
|---|---|---|---|
| 49 | (structure) | methane sulphonate | >230 |
| 50 | (structure) | methane sulphonate | >230 |
| 51 | (structure) | methane sulphonate | >230 |
| 52 | (structure) | methane sulphonate | 198–200 |
| 53 | (structure) | methane sulphonate | 218–222 |

| No. | compound | salt form | Mp. [° C.] |
|---|---|---|---|
| 54 | | | 144–147 |
| 55 | | methane sulphonate | 185–191 |
| 56 | | dichloride | 150–154 |
| 57 | | methane sulphonate | 220 |
| 58 | | di-methane sulphonate | 198–202 |

-continued
| No. | compound | salt form | Mp. [° C.] |
|---|---|---|---|
| 59 | 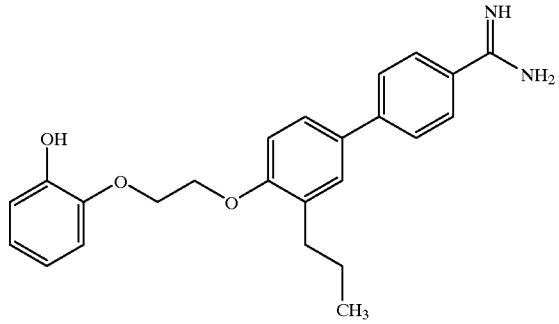 | chloride | 302 |
| 60 | 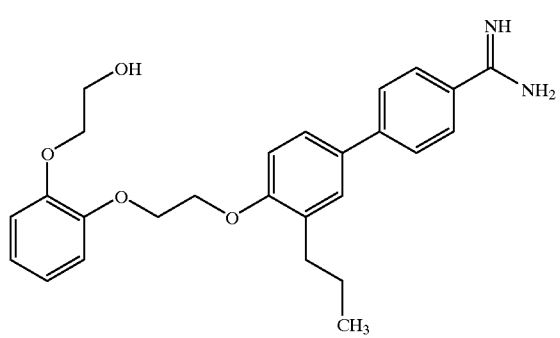 | methane sulphonate | 158 |
| 61 | 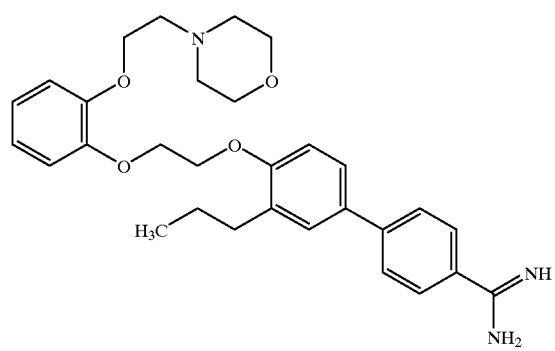 | methane sulphonate | 151 |
| 62 | 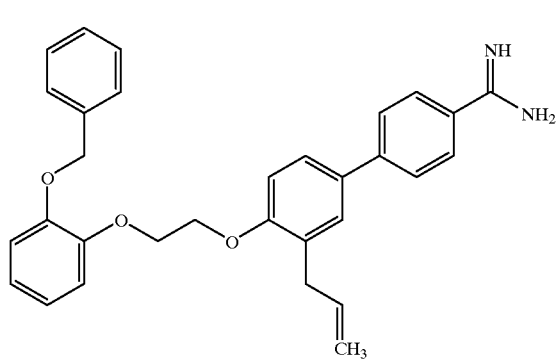 | chloride | 170–175 |

-continued
| No. | compound | salt form | Mp. [° C.] |
|---|---|---|---|
| 63 | 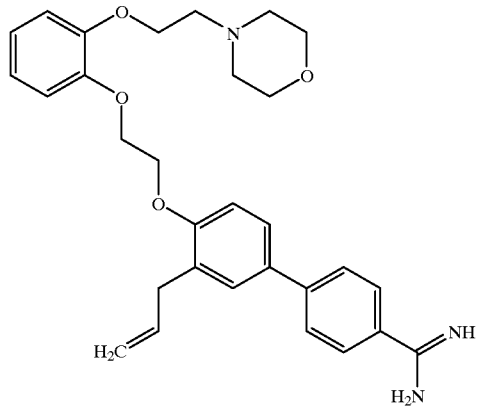 | methane sulphonate | 135–142 |
| 64 | 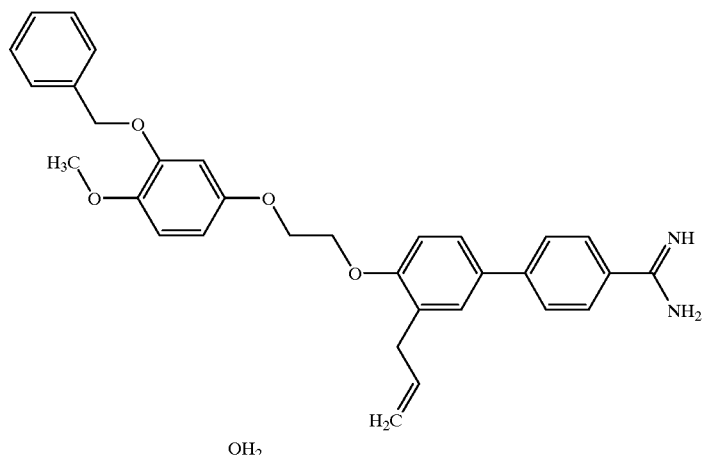 | chloride | 178 |
| 65 | 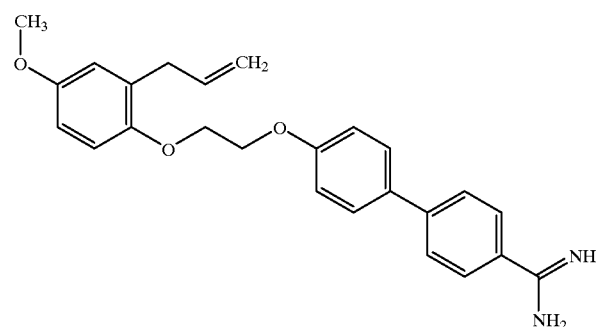 | chloride | 138–145 |
| 66 | 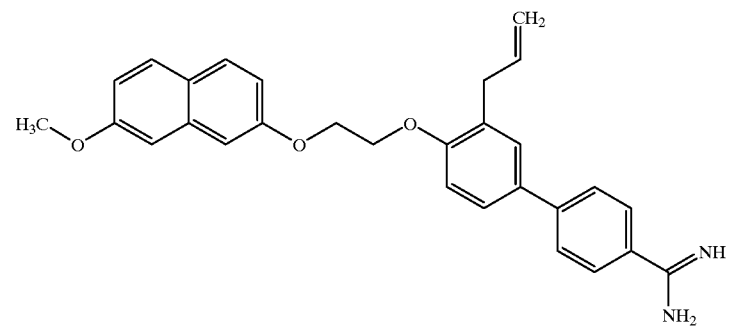 | chloride | 209–210 |

-continued

| No. | compound | salt form | Mp. [° C.] |
|---|---|---|---|
| 67 | | chloride | 182–183 |
| 68 | | chloride | 211–216 |
| 69 | | methane sulphonate | 168–175 |
| 70 | | methane sulphonate | 170–174 |

-continued

| No. | compound | salt form | Mp. [° C.] |
|---|---|---|---|
| 71 | | chloride | 159–161 |
| 72 | | chloride | 171–175 |
| 73 | | chloride | 180–188 |

| No. | compound | salt form | Mp. [° C.] |
|---|---|---|---|
| 74 | (structure) | chloride | 126–129 |
| 75 | (structure) | methane sulphonate | 158–166 |
| 76 | (structure) | methane sulphonate | 175–183 |

| No. | compound | salt form | Mp. [° C.] |
|---|---|---|---|
| 77 | 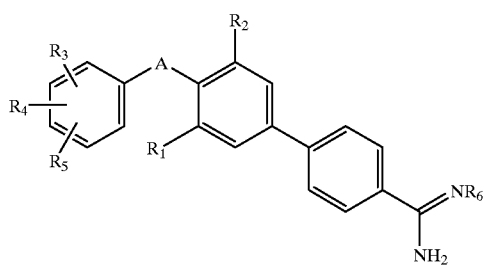 | methane sulphonate | |

What is claimed is:

1. A compound of the formula 1

(1)

wherein:

A is —O—$C_{2-4}$-alkyleneO— or —$C_{1-3}$-alkyleneO—;

$R_1$ is branched or unbranched $C_{1-6}$-alkyl, branched or unbranched $C_{3-6}$-alkenyl, F, Cl, Br or I;

$R_2$ is hydrogen, branched or unbranched $C_{1-6}$-alkyl, branched or unbranched $C_{3-6}$-alkenyl, F, Cl, Br or I;

$R_3$ and $R_4$ are, independently of one another, hydrogen, branched or unnbranched $C_{1-6}$-alkyl, branched or unbranched $C_{3-6}$-alkenyl, $C_{1-6}$-alkoxy, ($C_{1-4}$-alkyl)OC(O)O—, OH or $CF_3$, or $R_3$ and $R_4$ together denote a fused mono- or bicyclic ring system which is completely or partially conjugated and optionally has one or two heteroatoms selected from the group consisting of oxygen, sulphur and nitrogen, and which is optionally substituted by OH, $C_1$–$C_4$-alkoxy or $C_1$–$C_4$-alkyl;

$R_5$ is hydrogen, phenyl, —O-phenyl, —$CR_7R_8$-phenyl, —C(O)phenyl or —CH(OH)phenyl, wherein each of the foregoing phenyl moieties is optionally substituted by OH, $C_{1-4}$-alkoxy, or —C(O)$NR_9R_{10}$;

$R_6$ is hydrogen, $C_{1-6}$-alkoxycarbonyl, ($C_{1-5}$-alkyl)-carbonyl or —C(O)—O—($C_{1-6}$-alkylene)-$NR_{11}R_{12}$;

$R_7$ and $R_8$ are, independently of one another, hydrogen, branched or unnbranched $C_{1-8}$-alkyl, or $CF_3$;

$R_9$ and $R_{10}$ are, independently of one another, hydrogen or branched or unnbranched $C_{1-8}$-alkyl; and, $R_{11}$ and $R_{12}$ are, independently of one another, hydrogen or branched or unbranched $C_{1-8}$-alkyl;

or a pharmaceutically acceptable salt thereof.

2. A compound of the formula 1, in accordance with claim 1, wherein:

A is —O$CH_2CH_2$O—, —$CH_2$O— or —$CH_2CH_2CH_2$O—;

$R_1$ is branched or unnbranched $C_{1-5}$-alkyl or allyl;

$R_2$ is hydrogen;

$R_3$ is hydrogen, $C_{1-6}$-alkyl, $OCH_3$, $C_2H_5$OC(O)O—, OH, Cl, F or $CF_3$;

$R_4$ is hydrogen, —$OCH_3$ or OH; or, $R_3$ and $R_4$ together form a fused moiety which is a benzene ring, 3,4-dihydrocoumarin system or 1,3-dioxolane system, which fused moiety is optionally substituted by OH, $C_{1-3}$-alkyl or $OCH_3$;

$R_5$ is hydrogen, phenyl, —O-phenyl, —$CR_7R_8$-phenyl, wherein the foregoing phenyl moities are optionally substituted by OH or $OCH_3$, or $R_5$ is —C(O)$NR_9R_{10}$;

$R_6$ is hydrogen, $C_{1-4}$-alkoxycarbonyl or —C(O)—O—$(CH_2)_2$—N($C_2H_5)_2$;

$R_7$ and $R_8$ are, independently of one another, hydrogen, $CH_3$ or $CF_3$; and, $R_9$ and $R_{10}$ are, independently of one another, hydrogen or branched or unbranched $C_{1-8}$-alkyl;

or a pharmaceutically acceptable salt thereof.

3. A compound of the formula 2

(2)

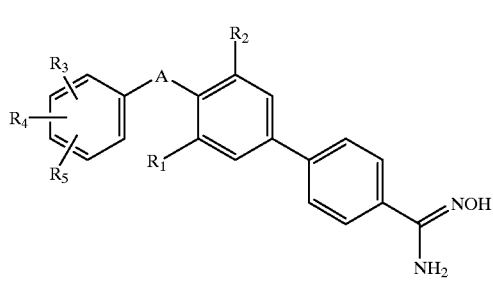

wherein:

A is —O—$C_{2-4}$-alkyleneO— or —$C_{1-3}$-alkyleneO—;

$R_1$ is branched or unbranched $C_{1-6}$-alkyl, branched or unbranched $C_{3-6}$-alkenyl, F, Cl, Br or I;

$R_2$ is hydrogen, branched or unbranched $C_{1-6}$-alkyl, branched or unbranched $C_{3-6}$-alkenyl, F, Cl, Br or I;

$R_3$ and $R_4$ are, independently of one another, hydrogen, branched or unnbranched $C_{1-6}$-alkyl, branched or unbranched $C_{3-6}$-alkenyl, $C_{1-6}$-alkoxy, $(C_{1-4}$-alkyl)OC(O)O—, OH or $CF_3$, or $R_3$ and $R_4$ together denote a fused mono- or bicyclic ring system which is completely or partially conjugated and optionally has one or two heteroatoms selected from the group consisting of oxygen, sulphur and nitrogen, and which is optionally substituted by OH, $C_{1-4}$-alkoxy or $C_1$–$C_4$-alkyl; and, $R_5$ is hydrogen, phenyl, —O-phenyl, —$CR_7R_8$-phenyl, —C(O)phenyl or —CH(OH)phenyl, wherein each of the foregoing phenyl moieties is optionally substituted by OH, $C_{1-4}$-alkoxy, or —$C(O)NR_9R_{10}$.

4. A process for making a compound of the formula 1

(1)

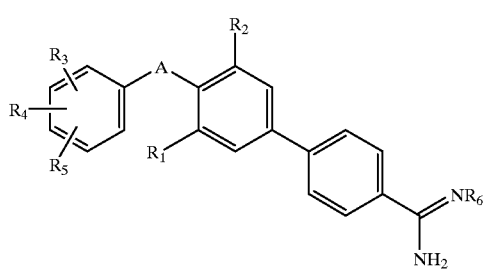

wherein:

A is —O—$C_{2-4}$-alkyleneO— or —$C_{1-3}$-alkyleneO—;

$R_1$ is branched or unbranched $C_{1-6}$-alkyl, branched or unbranched $C_{3-6}$-alkenyl, F, Cl, Br or I;

$R_2$ is hydrogen, branched or unbranched $C_{1-6}$-alkyl, branched or unbranched $C_{3-6}$-alkenyl, F, Cl, Br or I;

$R_3$ and $R_4$ are, independently of one another, hydrogen, branched or unnbranched $C_{1-6}$-alkyl, branched or unbranched $C_{3-6}$-alkenyl, $C_{1-6}$-alkoxy, $(C_{1-4}$-alkyl)OC(O)O—, OH or $CF_3$, or $R_3$ and $R_4$ together denote a fused mono- or bicyclic ring system which is completely or partially conjugated and optionally has one or two heteroatoms selected from the group consisting of oxygen, sulphur and nitrogen, and which is optionally substituted by OH, $C_1$–$C_4$-alkoxy or $C_1$–$C_4$-alkyl;

$R_5$ is hydrogen, phenyl, —O-phenyl, —$CR_7R_8$phenyl, —C(O)phenyl or —CH(OH)phenyl, wherein each of the foregoing phenyl moieties is optionally substituted by OH, $C_1$–$C_4$-alkoxy, or —$C(O)NR_9R_{10}$;

$R_6$ is hydrogen, $C_{1-6}$-alkoxycarbonyl, $(C_{1-5}$-alkyl)-carbonyl or —C(O)—O—$(C_{1-6}$-alkylene)—$NR_{11}R_{12}$;

$R_7$ and $R_8$ are, independently of one another, hydrogen, branched or unnbranched $C_{1-8}$-alkyl, or $CF_3$;

$R_9$ and $R_{10}$ are, independently of one another, hydrogen or branched or unnbranched $C_{1-8}$-alkyl; and, $R_{11}$ and $R_{12}$ are, independently of one another, hydrogen or branched or unbranched $C_{1-8}$-alkyl;

which process comprises reducing a compound of the formula 2

(2)

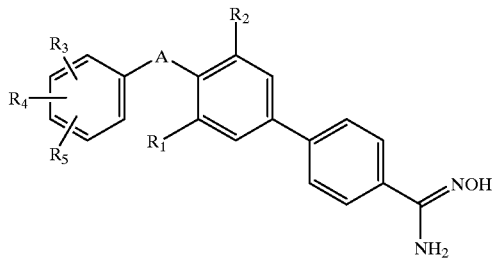

wherein A and $R_1$, $R_2$, $R_3$, $R_4$ and $R_5$ are as previously defined in this claim.

5. A process for making a compound of the formula 1

(1)

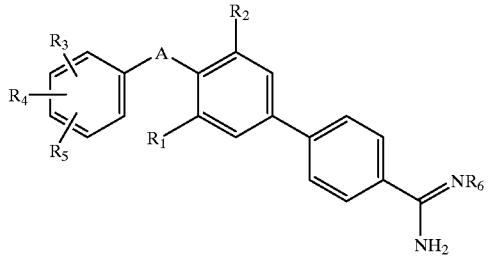

wherein:

A is —O—$C_{2-4}$-alkyleneO— or —$C_{1-3}$-alkyleneO—;

$R_1$ is branched or unbranched $C_{1-6}$-alkyl, branched or unbranched $C_{3-6}$-alkenyl, F, Cl, Br or I;

$R_2$ is hydrogen, branched or unbranched $C_{1-6}$-alkyl, branched or unbranched $C_{3-6}$-alkenyl, F, Cl, Br or I;

$R_3$ and $R_4$ are, independently of one another, hydrogen, branched or unnbranched $C_{1-6}$-alkyl, branched or unbranched $C_{3-6}$-alkenyl, $C_{1-6}$-alkoxy, $(C_{1-4}$-alkyl)OC(O)O—, OH or $CF_3$, or $R_3$ and $R_4$ together denote a fused mono- or bicyclic ring system which is completely or partially conjugated and optionally has one or two heteroatoms selected from the group consisting of oxygen, sulphur and nitrogen, and which is optionally substituted by OH, $C_1$–$C_4$-alkoxy or $C_1$–$C_4$-alkyl;

$R_5$ is hydrogen, phenyl, —O-phenyl, —$CR_7R_8$-phenyl, —C(O)phenyl or —CH(OH)phenyl, wherein each of the foregoing phenyl moieties is optionally substituted by OH, $C_{1-4}$-alkoxy, or —$C(O)NR_9R_{10}$;

$R_6$ is hydrogen, $C_{1-6}$-alkoxycarbonyl, $(C_{1-5}$-alkyl)-carbonyl or —C(O)—O—$(C_{1-6}$-alkylene)—$NR_{11}R_{12}$;

$R_7$ and $R_8$ are, independently of one another, hydrogen, branched or unnbranched $C_{1-8}$-alkyl, or $CF_3$;

$R_9$ and $R_{10}$ are, independently of one another, hydrogen or branched or unnbranched $C_{1-8}$-alkyl; and, $R_{11}$ and $R_{12}$ are, independently of one another, hydrogen or branched or unbranched $C_{1-8}$-alkyl;

which process comprises reacting a compound of the formula 3

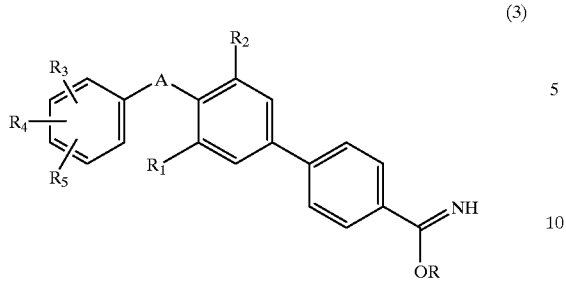

(3)

wherein A and $R_1$, $R_2$, $R_3$, $R_4$ and $R_5$ are as previously defined in this claim with ammonia.

6. A process for making a compound of the formula 1

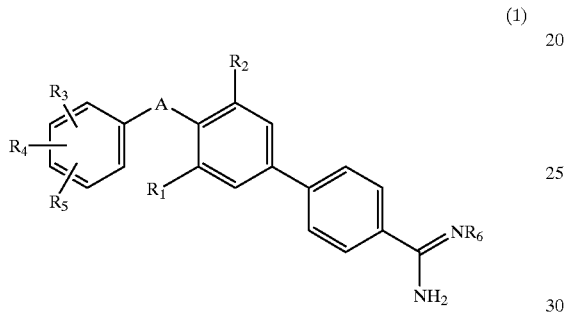

(1)

wherein:

A is —O—$C_{2-4}$-alkyleneO— or —$C_{1-3}$-alkyleneO—;

$R_1$ is branched or unbranched $C_{1-6}$-alkyl, branched or unbranched $C_{3-6}$-alkenyl, F, Cl, Br or I;

$R_2$ is hydrogen, branched or unbranched $C_{1-6}$-alkyl, branched or unbranched $C_{3-6}$-alkenyl, F, Cl, Br or I;

$R_3$ and $R_4$ are, independently of one another, hydrogen, branched or unnbranched $C_{1-6}$-alkyl, branched or unbranched $C_{3-6}$-alkenyl, $C_{1-6}$-alkoxy, ($C_{1-4}$-alkyl)OC(O)O—, OH or $CF_3$, or $R_3$ and $R_4$ together denote a fused mono- or bicyclic ring system which is completely or partially conjugated and optionally has one or two heteroatoms selected from the group consisting of oxygen, sulphur and nitrogen, and which is optionally substituted by OH, $C_1$–$C_4$-alkoxy or $C_1$–$C_4$-alkyl;

$R_5$ is hydrogen, phenyl, —O-phenyl, —$CR_7R_8$-phenyl, —C(O)phenyl or —CH(OH)phenyl, wherein each of the foregoing phenyl moieties is optionally substituted by OH, $C_{1-4}$-alkoxy, or —C(O)$NR_9R_{10}$;

$R_6$ is hydrogen, $C_{1-6}$-alkoxycarbonyl, ($C_{1-5}$-alkyl)-carbonyl or —C(O)—O—($C_{1-6}$-alkylene)—$NR_{11}R_{12}$;

$R_7$ and $R_8$ are, independently of one another, hydrogen, branched or unnbranched $C_{1-8}$-alkyl, or $CF_3$;

$R_9$ and $R_{10}$ are, independently of one another, hydrogen or branched or unnbranched $C_{1-8}$-alkyl; and, $R_{11}$ and $R_{12}$ are, independently of one another, hydrogen or branched or unbranched $C_{1-8}$-alkyl;

which process comprises reacting a compound of the formula 4

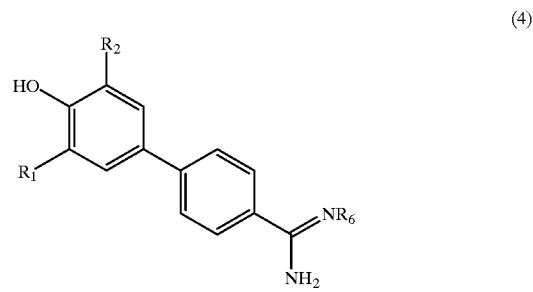

(4)

wherein $R_1$, $R_2$ and $R_6$ are as previously defined in this claim with a compound of the formula 5

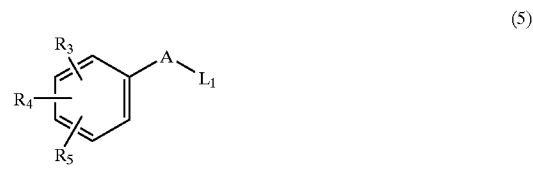

(5)

wherein A and $R_3$, $R_4$ and $R_5$ are as previously defined in this claim and $L_1$ is a nucleofugal leaving group, in an aprotic solvent.

7. A process for making a compound of the formula 1

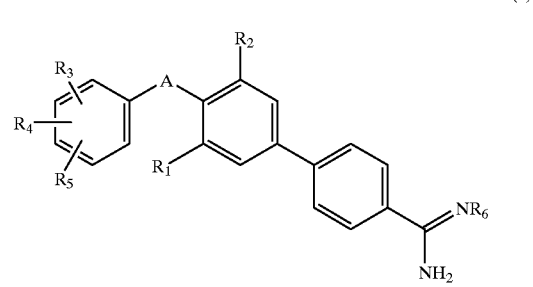

(1)

wherein:

A is —O—$C_{2-4}$-alkyleneO— or —$C_{1-3}$-alkyleneO—;

$R_1$ is branched or unbranched $C_{1-6}$-alkyl, branched or unbranched $C_{3-6}$-alkenyl, F, Cl, Br or I;

$R_2$ is hydrogen, branched or unbranched $C_{1-6}$-alkyl, branched or unbranched $C_{3-6}$-alkenyl, F, Cl, Br or I;

$R_3$ and $R_4$ are, independently of one another, hydrogen, branched or unnbranched $C_{1-6}$-alkyl, branched or unbranched $C_{3-6}$-alkenyl, $C_{1-6}$-alkoxy, ($C_{1-4}$-alkyl)OC(O)O—, OH or $CF_3$, or $R_3$ and $R_4$ together denote a fused mono- or bicyclic ring system which is completely or partially conjugated and optionally has one or two heteroatoms selected from the group consisting of oxygen, sulphur and nitrogen, and which is optionally substituted by OH, $C_1$–$C_4$-alkoxy or $C_1$–$C_4$-alkyl;

$R_5$ is hydrogen, phenyl, —O-phenyl, —$CR_7R_8$-phenyl, —C(O)phenyl or —CH(OH)phenyl, wherein each of the foregoing phenyl moieties is optionally substituted by OH, $C_{1-4}$-alkoxy, or —C(O)$NR_9R_{10}$;

$R_6$ is hydrogen, $C_{1-6}$-alkoxycarbonyl, ($C_{1-5}$-alkyl)-carbonyl or —C(O)—O—($C_{1-6}$-alkylene)—$NR_{11}R_{12}$;

$R_7$ and $R_8$ are, independently of one another, hydrogen, branched or unnbranched $C_{1-8}$-alkyl, or $CF_3$;

$R_9$ and $R_{10}$ are, independently of one another, hydrogen or branched or unnbranched $C_{1-8}$-alkyl; and, $R_{11}$ and $R_{12}$ are, independently of one another, hydrogen or branched or unbranched $C_{1-8}$-alkyl;

which process comprises reacting a compound of the formula 6

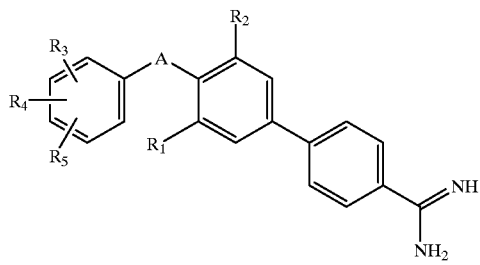

(6)

wherein A, $R_1$, $R_2$, $R_3$, $R_4$ and $R_5$ are as previously defined in this claim with a compound of the formula 7

$$L_2-R_6'$$ (7)

wherein $R_6'$ is $C_1$–$C_6$-alkoxycarbonyl or $C_1$–$C_6$-acyl and $L_2$ is a nucleofugal leaving group.

8. A pharmaceutical composition comprising a compound of the formula 1, in accordance with claims 1 or 2, and a pharmaceutically acceptable carrier.

9. A method for treating arthritis, asthma, chronic obstruct lung disease, psoriasis, ulcerative colitis, gastropathy or enteropathy induced by nonsteroidal antiinflammatories, cystic fibrosis, Alzheimer's disease, shock, reperfusion damage/ischaemia, atherosclerosis or multiple sclerosis which comprises administering to a patient in need of such treatment a therapeutically effective amount of a compound of the formula 1, in accordance with claims 1 or 2.

* * * * *